US011712413B2

United States Patent
Huang et al.

(10) Patent No.: US 11,712,413 B2
(45) Date of Patent: Aug. 1, 2023

(54) HALOBACILLUS TRUEPERI TCI66207 AND BACTERIAL LYSATE THEREOF AND USE OF BACTERTAL LYSATE

(71) Applicant: TCI CO., LTD., Taipei (TW)

(72) Inventors: Chu-Han Huang, Taipei (TW); Yung-Hsiang Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 316 days.

(21) Appl. No.: 16/932,867

(22) Filed: Jul. 20, 2020

(65) Prior Publication Data
US 2021/0015736 A1 Jan. 21, 2021

Related U.S. Application Data

(60) Provisional application No. 62/875,997, filed on Jul. 19, 2019.

(51) Int. Cl.
| | |
|---|---|
| A61Q 19/00 | (2006.01) |
| A61Q 19/08 | (2006.01) |
| A23L 33/135 | (2016.01) |
| A61K 35/747 | (2015.01) |
| A61P 17/00 | (2006.01) |
| C12N 1/20 | (2006.01) |
| A61K 8/99 | (2017.01) |

(52) U.S. Cl.
CPC .............. *A61K 8/99* (2013.01); *A61Q 19/007* (2013.01)

(58) Field of Classification Search
CPC .... A61K 8/99; A61K 2800/78; A61K 35/747; A61Q 19/007; A61Q 19/00; A61Q 19/08; A23L 33/135; A61P 17/00; A23V 2002/00; A23Y 2220/63; C12N 1/205; C12R 2001/225

See application file for complete search history.

(56) References Cited

FOREIGN PATENT DOCUMENTS

WO 2009127057 A1 10/2009

OTHER PUBLICATIONS

BIO Asia-Taiwan International Conference & Exhibition: Explore the Future—TCI Academic Seminar., https://www.rocaic.org/news_detail.php?id=1310, web page uploaded before Jul. 20, 2018 and were retrieved on Jul. 28,2021 Full Text.
Non-traditional producers of microbial exopolysaccharides., T.P. Pirog et al., Biotechnologia Acta, p. 5-27, vol. 11, No.4, 2018 p. 17.

*Primary Examiner* — Renee Claytor
*Assistant Examiner* — Ryshonda Patrice Lewis
(74) *Attorney, Agent, or Firm* — Chieh-Mei Wang

(57) ABSTRACT

A *Halobacillus trueperi* TCI66207 strain, deposited in the Leibniz Institute DSMZ-German Collection of Microorganisms and Cell Cultures (Accession number DSM 33381). The *H. trueperi* TCI66207 strain has one or more of the following function: improving skin cell mitochondrion activity, promoting skin cell proliferation, maintaining skin corneum layer completeness, increasing expression of keratin (Keratin14) and/or hyaluronic acid synthase (HAS3) genes and promoting hyaluronic acid production.

6 Claims, 6 Drawing Sheets
Specification includes a Sequence Listing.

0th week

4th week

0th week

4th week

HALOBACILLUS TRUEPERI TCI66207 AND BACTERIAL LYSATE THEREOF AND USE OF BACTERTAL LYSATE

CROSS-REFERENCE TO RELATED APPLICATION

This application claims the benefit of U.S. provisional application Ser. No. 62/875,997, filed on Jul. 19, 2019. The entirety of the above-mentioned patent application is hereby incorporated by references herein and made a part of the specification.

REFERENCE OF AN ELECTRONIC SEQUENCE LISTING

The contents of the electronic sequence listing (TCI66207_0720_ST25.tet; Size:3.4 KB; and Date of Creation: Jul. 20, 2020) is herein incorporated by reference in its entirety.

BACKGROUND

Technical Field

The present invention relates to *Halobacillus trueperi*, more particularly to a *H. trueperi* TCI66207 strain and bacterial lysate thereof and use of the bacterial lysate.

Related Art

Skin is a first line of defense of a human body to isolate damage in an external environment, such as ultraviolet rays, pathogens and friction, and to prevent water loss. The skin sequentially includes an epidermal layer, a dermal layer mainly formed by connective tissues, and subcutaneous tissues from outside to inside. The epidermal layer is an outermost layer of the skin and is constantly renewed. When skin cells are damaged, or a proliferation rate of skin cells is reduced, skin moisture loss easily occurs. If a collagen network of the skin is damaged, a skin aging phenomenon (such as wrinkles, sag, darkness and dryness) is further caused.

The epidermal layer and the dermal layer include collagen, elastin and hyaluronic acid, which provide support power and skin elasticity. However, when the collagen, elastin and hyaluronic acid decrease along with age increase, these factors may all reduce skin fullness and elasticity.

Additionally, a main ingredient of a corneum layer is keratin, and can secret substances such as hyaluronic acid as intercellular substances, so as to maintain structure completeness of a skin barrier of the epidermal layer and adsorb water to keep the skin moist, thereby preventing skin water loss and forming complete protection. When the skin is stimulated by an external environment, causing keratinocytes to be unable to maintain a normal metabolism cycle, the water holding ability of the skin decreases, the epidermal layer barrier of the skin is damaged, and the skin turns to be rough, dry, desquanative, weak, excitable, sensitive and red, so that the health and water holding ability of the corneum layer are really very important on external damage resistance.

SUMMARY

In view of this, the present invention provides a *H. trueperi* TCI66207 strain and bacterial lysate thereof and use of the bacterial lysate.

In some embodiments, a *H. trueperi* TCI66207 strain is deposited in Non-profit Private Entity Food Industry Research and Development Institute (Deposit number: BCRC910961).

In some embodiments, a composition includes the bacterial lysate of the *H. trueperi* TCI66207 strain.

In some embodiments, use of the bacterial lysate of the *H. trueperi* TCI66207 strain for preparing a composition for maintaining skin corneum layer completeness and/or promoting hyaluronic acid production is provided.

The *H. trueperi* TCI66207 strain in any one embodiment is deposited in Non-profit Private Entity Food Industry Research and Development Institute (Deposit number: BCRC910961). In some embodiments, the bacterial lysate of the *H. trueperi* TCI66207 strain has a function of improving skin cell mitochondrion activity. In some other embodiments, the bacterial lysate of the *H. trueperi* TCI66207 strain has a function of promoting cell proliferation. In some other embodiments, the bacterial lysate of the *H. trueperi* TCI66207 strain has a function of maintaining skin corneum layer completeness and/or promoting hyaluronic acid production. In some other embodiments, the bacterial lysate of the *H. trueperi* TCI66207 strain increases expression of keratin (Keratin14) and/or hyaluronic acid synthase (HAS3) genes.

Therefore, in some embodiments, the bacterial lysate of the *H. trueperi* TCI66207 strain may be used for preparing a composition for maintaining skin corneum layer completeness and/or promoting hyaluronic acid production. In some other embodiments, the bacterial lysate of the *H. trueperi* TCI66207 strain is used for preparing a composition for improving skin cell mitochondrion activity. In some other embodiments, the bacterial lysate of the *H. trueperi* TCI66207 strain is used for preparing a composition for promoting cell proliferation.

DETAILED DESCRIPTION

Figure 1:
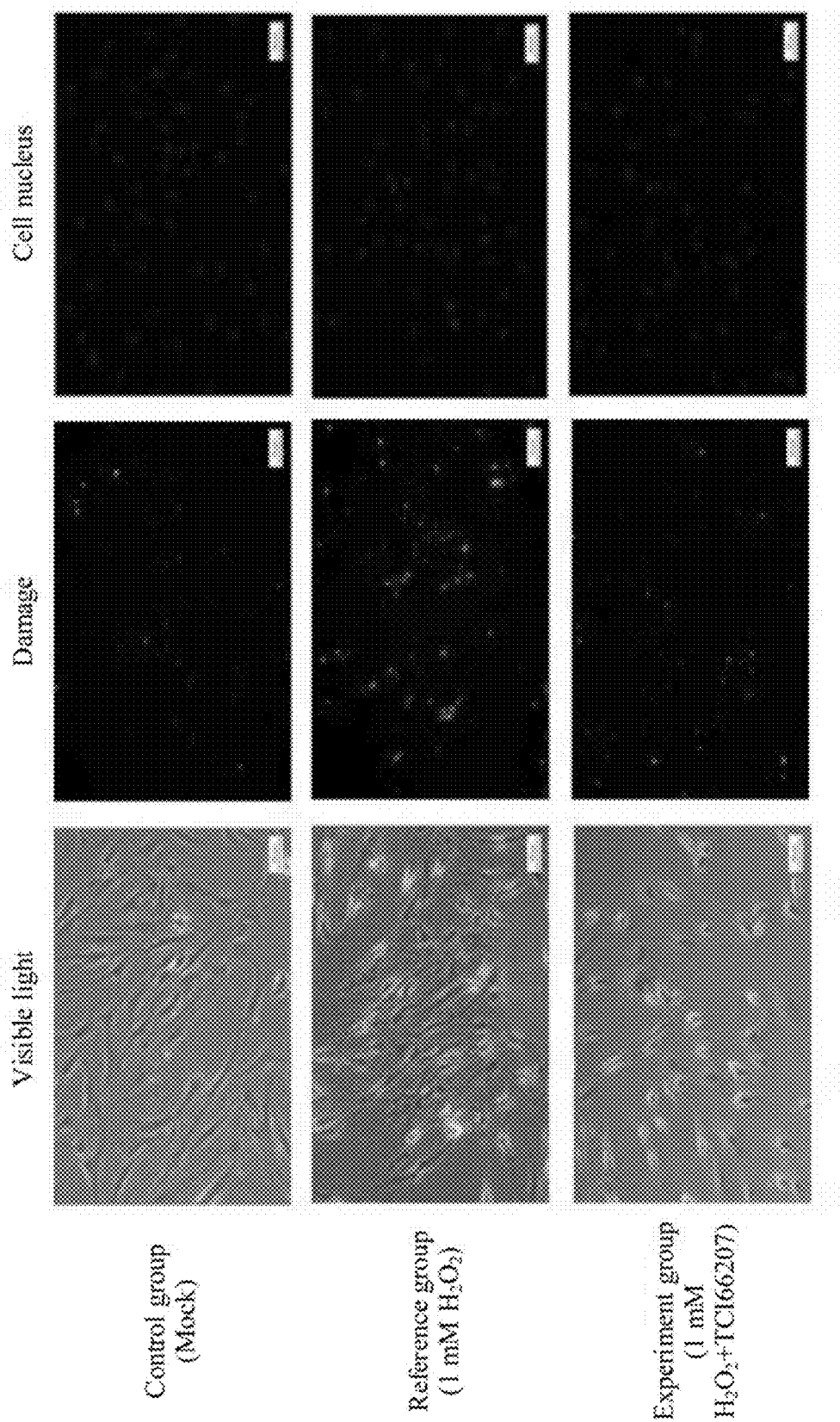
FIG. 1 shows levels of damage of human skin fibroblasts in different groups observed by a fluorescence microscope (purchased from ZEISS).

As used herein, a concentration symbol "wt %" generally refers to weight percent concentration, and a concentration symbol "vol %" generally refers to volume percent concentration.

In the figures "*" represents a p value less than 0.05, "" represents a p value less than 0.01, and "*" represents a p value less than 0.001. More "*" represents more significant statistical differences.

In some embodiments, a *H. trueperi* TCI66207 strain is a strain isolated from seawater at a depth of 662 m in Pacific Ocean at the east coast of Taiwan. The *H. trueperi* TCI66207 is deposited in Non-profit Private Entity Food Industry Research and Development Institute, and has a deposit number of BCRC910961. *H. trueperi* TCI66207 is gram-positive bacilli, grows in a high-salt-concentration environment, and is heterotroph. Here, a growth temperature of the *H. trueperi* TCI66207 is 25° C., and the *H. trueperi* TCI66207 can survive at a salinity of 2.5% sodium chloride (NaCl). *Halobacillus trueperi* TCI66207 strain is deposited in the Leibniz Institute DSMZ-German Collection of Microorganisms and Cell Cultures (Address: Inhoffenstr. 7 B D-38124 Braunschweig), Germany, in accordance with the Budapest Treaty, on Feb. 25, 2021, and has an accession number of DSM 33381.

In some embodiments, a composition includes bacterial lysate of the *H. trueperi* TCI66207 strain.

In some embodiments, the bacterial lysate of the *H. trueperi* TCI66207 strain has a function of improving skin cell mitochondrion activity.

In some embodiments, the bacterial lysate of the *H. trueperi* TCI66207 strain has a function of promoting skin cell proliferation.

In some embodiments, the bacterial lysate of the *H. trueperi* TCI66207 strain has a function of maintaining skin corneum layer completeness and/or promoting hyaluronic acid production.

In some embodiments, the bacterial lysate of the *H. trueperi* TCI66207 strain increases expression of keratin (Keratin14) and/or hyaluronic acid synthase (HAS3) genes.

In some embodiments, use of the bacterial lysate of the *H. trueperi* TCI66207 strain for preparing a composition for maintaining skin corneum layer completeness and/or promoting hyaluronic acid production is provided.

In some embodiments, the bacterial lysate of the *H. trueperi* TCI66207 strain increases expression of keratin (Keratin14) and/or hyaluronic acid synthase (HAS3) genes.

In some embodiments, use of the bacterial lysate of the *H. trueperi* TCI66207 strain for preparing a composition for improving skin cell mitochondrion activity is provided.

In some embodiments, use of the bacterial lysate of the *H. trueperi* TCI66207 strain for preparing a composition for promoting skin cell proliferation is provided.

In some embodiments, the above compositions may be applied to an individual in a form such as powder, granules, liquid, gel or cream in a skin coating mode. The above compositions may be made into food, beverages, nutritional supplements or medicines to be applied to an individual in an oral mode.

Strain Identification

The *H. trueperi* TCI66207, an isolated strain isolated from seawater at a depth of 662 m in Pacific Ocean at the east coast of Taiwan, was subjected to strain identification by 16S ribosomal gene (16SrDNA) of *Halobacillus halophilus*. A 16S ribosomal gene (16SrDNA) sequence (i.e., SEQ ID NO:1) of the isolated strain was obtained through polymerase chain reaction (PCR). Then, after the SEQ ID NO:1 sequence was compared with 16S ribosomal gene (16SrDNA) sequences of subspecies of other *H. trueperi* according to a US National Center for Biotechnology Information (NCBI) website, it could be known that the *H. trueperi* TCI66207 was a *H. trueperi* strain. Moreover, *Halobacillus trueperi* TCI66207 strain was deposited in the Leibniz Institute DSMZ-German Collection of Microorganisms and Cell Cultures (Address: Inhoffenstr. 7 B D-38124 Braunschweig), Germany, in accordance with the Budapest Treaty, on Feb. 25, 2021, and had an accession number of DSM 33381.

Example 1: Preparation of Bacterial Lysate of TCI66207

The *H. trueperi* TCI66207 strain was taken out from a cryopreservation tube, was inoculated into a medium at 10 vol %, and was cultured at 25° C. for three days to obtain bacterial liquid.

The medium included 10 vol % of yeast extracts (purchased from BD Pharminge company, model number: BD Bacto™212750), 0.09 vol % of dipotassium phosphate ($K_2HPO_4$) (purchased from Sigma-Aldrich company, model number: P5656), 0.43 vol % of magnesium sulfate ($MgSO_4$) (purchased from Sigma-Aldrich company, model number: 63138), 0.2 vol % of glucose (purchased from Sigma-Aldrich company, model number: G7021) and 2.5 vol % of sodium chloride (purchased from Sigma-Aldrich company, model number: S7653).

Then, the bacterial liquid was centrifuged for 15 min at a rotating speed of 5000 rpm/min. Supernatant was removed and bacterial sludge was collected. Water with a weight being 9 times of that of the bacterial sludge was added. The bacterial sludge was uniformly suspended to obtain a solution A.

Then, breaking was performed by a repeated freeze-thaw method. The repeated freeze-thaw method includes the following step: the solution A was put in a −80° C. environment for 20 min, and then, the solution A was put in a 95° C. environment for 5 min. This step was repeated for 5 times to obtain a solution B.

Then, the solution B was centrifuged for 15 min at a rotating speed of 5000 rpm/min. Upper layer clear bacterial lysate was taken to be used as a sample A. 0.25 mL of the sample A (clear bacterial lysate) and 99.75 mL of water were mixed to be used as a sample B of a cell experiment. In other words, a concentration of the sample B is 0.25 vol %.

Example 2: Cell Experiment: Test Skin's Antioxidant Capacity with Fluorescent Damage Staining Human skin fibroblasts (CCD-966sk, BCRC No. 60153) were cultured in a 24-well culture tray. 3 mL of a cell medium was added in each well. $2\times10^4$ human skin fibroblasts were planted in each well. Overnight (24 h) culture was performed in a 37° C. constant-temperature incubator.

The cell medium was a 90 vol % minimum essential medium Eagle (prepared in Earle's balanced salt solution (Earle's BSS)) added with 1.5 g of sodium bicarbonate, 1 mM (mmol/L) of sodium pyruvate and 10 vol % of fetal bovine serum (purchased from Gibco company) per one liter.

The above cultured human skin fibroblasts were divided into the following three groups: Experiment group, Reference group and Control group. Experiment group: after 0.01 mL of the sample B (bacterial lysate of TCI66207) was added into per one milliliter of the cell medium in the culture tray, the above human skin fibroblasts were cultured for 24 h, and then, 1 mM (mmol/L) of hydrogen peroxide ($H_2O_2$) was added for culture for 30 min. Reference group: the above human skin fibroblasts were cultured for 24 h without being added with the sample B, and then, 1 mM (mmol/L) of hydrogen peroxide ($H_2O_2$) was added for culture for 30 min. Control group: the above human skin fibroblasts were cultured for 24 h and 30 min without being added with the sample B and the hydrogen peroxide.

After a prodidium iodide (PI) reagent (purchased from BD Pharminge company, model number Cat. 51-66211E) was purchased and obtained, a volume was diluted by 250 times to obtain a PI solution. After annexin V (purchased from eBioscience company, model number Cat. 00-0055-43) was purchased and obtained, a volume was diluted by 250 times by an annexin V binding buffer solution (purchased from eBioscience, model number: Cat. 00-0055-43) to obtain an annexin V solution. After the above step of culturing the human skin fibroblasts, each group was stained for 15 to 30 min by the PI reagent and the annexin V solution.

Then, each group used a Hoechst 33342 solution for staining cells for 3 min. Then, each group used a phosphate buffer solution (PBS) (purchased from Gibo company) for washing the cells twice. Here, after a Hoechst 33342 reagent (purchased from Thermo company, model number: Cat. 62249) was purchased and obtained, a volume is diluted by 20000 times to obtain a Hoechst solution.

Referring to FIG. 1, the obtained stained cells were observed by a fluorescence microscope (purchased from ZEISS). In an early period of cell apoptosis, phosphatidylserine turned to the outside from the inside of membrane lipid. The annexin V was a calcium ion dependent phospholipid binding protein capable of realizing specific binding with phosphatidylserine. The PI reagent was a nucleic acid dye. Therefore, the cells stained by the annexin V solution and the PI solution were damaged cells or dead cells. Green fluorescence represented cells stained by the annexin V solution. Blue fluorescence represented cells stained by the PI solution.

From results in FIG. 1, it could be known that after the damaged human skin fibroblasts were treated by the sample B (bacterial lysate of TCI66207), a quantity of cells stained by the annexin V solution and the PI solution was smaller than a quantity of cells not treated by the sample B. That is, after the damaged human skin fibroblasts were treated by the sample B, the level of degree might be reduced.

Example 3: Cell Experiment-Skin Cell Mitochondrion Activity Experiment

Mitochondria are cell organs supplying energy to cells, and participate in cell oxidation-reduction constancy and nutrient metabolism. The normal operation of the mitochondria is very important on maintaining cell vitality and proliferation ability. To discuss the influence of the bacterial lysate of the *H. trueperi* TCI66207 strain on functions of the skin cell mitochondria, the present embodiment used a flow cytometry to evaluate the mitochondria activity change of the human skin fibroblasts CCD-966SK after the human skin fibroblasts CCD-966SK were treated by the bacterial lysate of the *H. trueperi* TCI66207 strain.

Firstly, the human skin fibroblasts (CCD-966sk, BCRC No. 60153) were cultured in a 6-well culture tray. 0.01 mL of a cell medium was added in each well. $1 \times 10^5$ human skin fibroblasts were planted in each well. Overnight (24 h) culture was performed in a 37° C. constant-temperature incubator. The cell medium of this example was identical to the cell medium in Example 2, so the descriptions thereof are omitted herein.

The above cultured human skin fibroblasts were divided into the following two groups: Experiment group and Control group. Experiment group: after 0.01 mL of the sample B (bacterial lysate of TCI66207) was added in the culture tray, the human skin fibroblasts were cultured for 24 h. Control group: the cell medium was not added with the sample B. and the human skin fibroblasts were cultured for 24 h.

Then, the cells in each group were washed twice by a phosphate buffer solution (1×PBS) (purchased from Gibo company). Then, each group was added with 200 μL of trypsin (purchased from UNI-ONWARD company) to react for 5 min at a room temperature (25° C.), so that the cells fell off from the culture tray, and the cells were collected to a 15 mL test tube previously used to collect the culture solution. The test tube was centrifuged for 5 min at 300 g to form supernatant and cell precipitates. The supernatant was removed. Then, in a darkroom, the cell precipitates in each group were re-dissolved again by 1 mL of phosphate buffer solution (1×PBS) to form a cell suspension.

Next, a BDTM MitoScreen (JC-1, model number: Cat. 551302) mitochondrion specific reagent was added into each group of cell suspension for staining for 15 min. Then, the cells in each group were washed twice by the phosphate buffer solution (PBS). The membrane potential change of the cell mitochondria was analyzed and observed by a flow cytometry (purchased from BD Pharmingen company, model number: BDTM Accuri C6 Plus), and mitochondrion activity analysis was performed.

Figure 2:
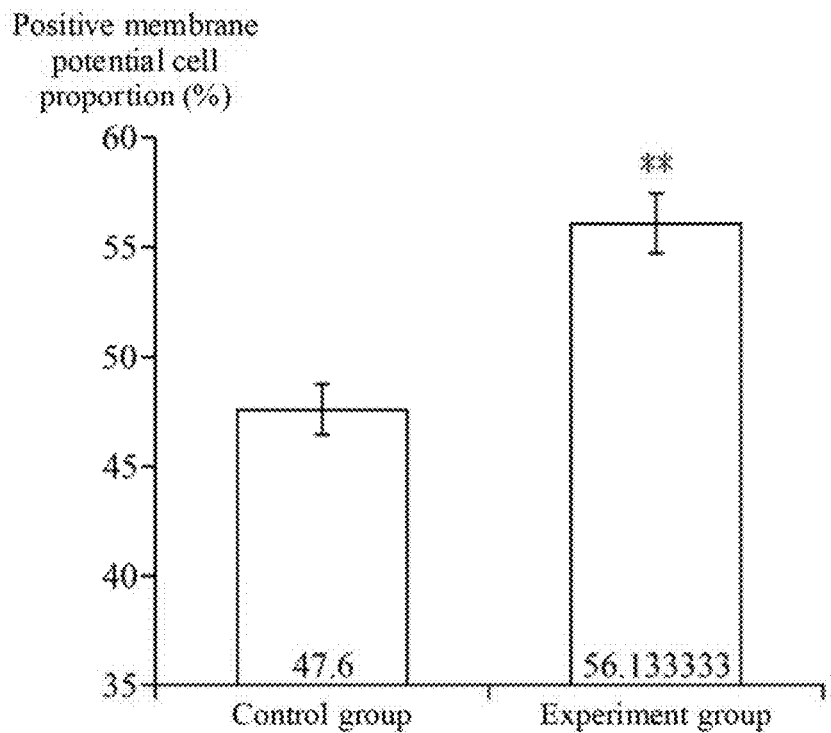
FIG. 2 shows that bacterial lysate of a *H. trueperi* TCI66207 strain can improve skin cell mitochondrion activity.

From results in FIG. 2, after Experiment group was treated by the sample B (bacterial lysate of TCI66207), a positive membrane potential cell proportion of Experiment group was about 56.133%, and a positive membrane potential cell proportion of Control group was about 47.6%. In other words, compared with Control group, Experiment group realized obvious improvement of the human skin fibroblast cell mitochondrion activity. It showed that the bacterial lysate of the *H. trueperi* TCI66207 strain of the embodiment of the present invention could improve the skin cell mitochondrion activity, thereby improving skin cell activity. In the figures, * represents a P value <0.05.  represents a P value <0.01. * represents a P value <0.001.

Example 4: Cell Experiment-Cell Proliferation Experiment

The human skin fibroblasts (CCD-966sk, ATCC®CRL-1881™) were cultured in a 6-well culture tray. 3 mL of a cell medium (purchased from Gibco company) was added in each well. The cell medium was a minimum essential medium (purchased from Gibco company), and included 10 vol % of fetal bovine serum (FBS) (purchased from Gibco company), 1 vol % of penicillin/streptomycin (purchased from Gibco company) and 1 mM (mmol/L) of sodium pyruvate relative to the cell medium (purchased from Gibco company). $1\times10^5$ human skin fibroblasts were planted in each well. Overnight (24 h) culture was performed in a 37° C. constant-temperature incubator.

The above cultured human skin fibroblasts were divided into the following three groups: Experiment group, Reference group and Control group. Experiment group: after 0.01 mL of the sample B (bacterial lysate of TCI66207) was added to per one milliliter of cell medium in the culture tray, the human skin fibroblasts were cultured for 24 h. Reference group: the above human skin fibroblasts were cultured for 24 h after being added with 10 vol % FBS (purchased from Gibco company). Control group: the cell medium was not added with the sample B and the FBS, and the human skin fibroblasts were cultured for 24 h.

Then, cell proliferation analysis was subsequently performed according to a standard process of cell proliferation assay kits (Click-iT™ Plus EdU Flow Cytometry Assay Kits-Alexa Fluor™ 488 picolyl azide, 50 tests) (purchased from Invitrogen company, model number: C10632). 10 µM of a thymidine analogue (5-ethynyl-2'-deoxyuridine, referred to as EdU hereinafter) relative to the medium was added into each group, and then, cells in each group were subsequently cultured for 1 to 2 h.

Then, the cell medium was removed. 0.5 vol % of trypsin (purchased from UNI-ONWARD company) was added, so that the cells fell off from the culture tray, and the cells were collected. Then, the cells in each group were washed once by a phosphate buffer solution (PBS) (purchased from UNI-ONWARD company) containing 1 vol % of fetal bovine serum protein (BSA). Then, 100 µl of Click-iT™ fixative was added for immobilizing the cells. The cells were put at a room temperature (25° C.) for light-avoiding treatment for 15 min. Then, the cells in each group were washed by the phosphate buffer solution (PBS) (purchased from UNI-ONWARD company) containing 1 vol % of fetal bovine serum protein (BSA). Then, 100 µl of Click-iT™ saponin-based permeabilization and wash reagent was added. The cells were put at a room temperature (25° C.) for light-avoiding treatment for 15 min.

Then, a cocktail reaction reagent (Click-iT™ Plus reaction cocktail) was prepared according to cell proliferation assay kits (Click-iT™ Plus EdU) (purchased from Invitrogen™ company, model number: C10632) to prepare Click-iT™ reaction. It should be noted that the cocktail reaction reagent needed to be completely used within 15 min after the preparation.

The prepared cocktail reaction reagent (Click-iT™ Plus reaction cocktail) was added into the cells in each group, and the cells were put at a room temperature (25° C.) for light-avoiding treatment for 30 min.

Then, the cells in each group were washed by a Click-iT™ saponin-based permeabilization solution. Supernatant was removed. Re-dissolution was performed by 500 µL of Click-iT™ saponin-based permeabilization.

Figure 3:
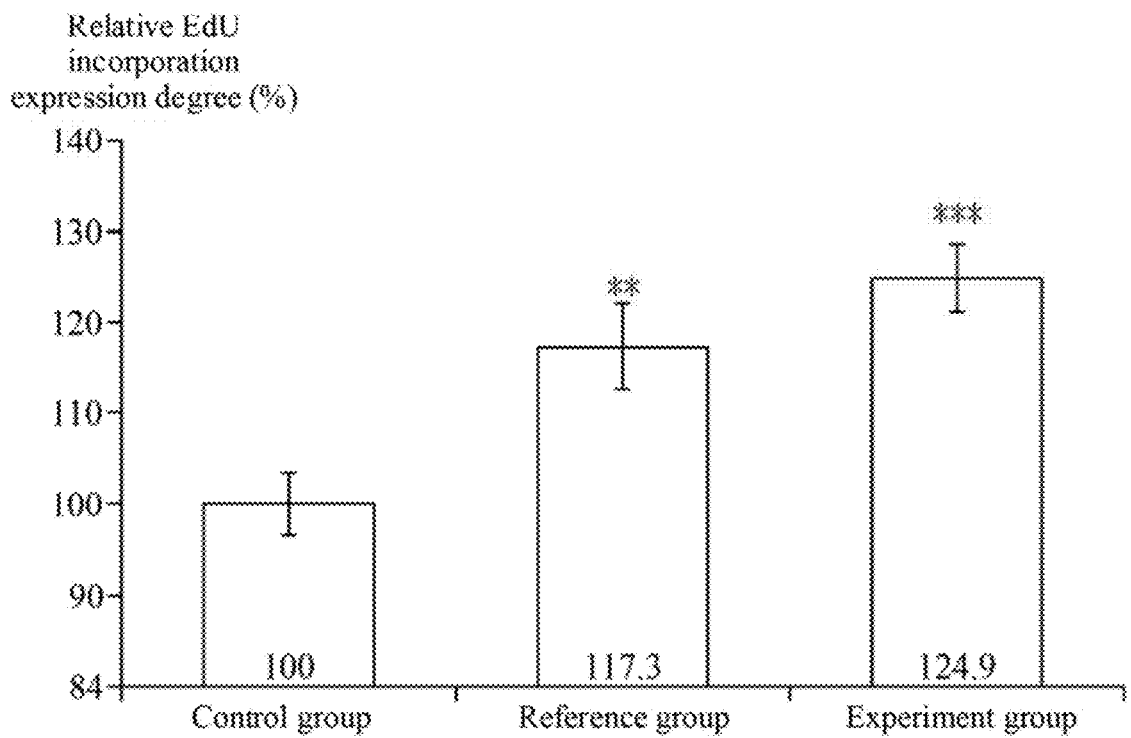
FIG. 3 shows that bacterial lysate of the *H. trueperi* TCI66207 strain can promote skin cell proliferation.

Next, a flow cytometry (purchased from BD Pharmingen company) was used for treatment by 488 nm excitation light and 530 nm emission light. For measured values, statistical significance of two measured values was analyzed by Student-t test through Microsoft EXCEL software. Results were as shown in FIG. 3. Experiment group and Reference group was compared with Control group. * represents a P value <0.05.  represents a P value <0.01. * represents a P value <0.001.

From FIG. 3, it could be known that the relative EdU incorporation times of Experiment group added with the sample B (bacterial lysate of TCI66207) were significantly increased. The skin cell proliferation percentage was increased by 24.9% through being compared with that of Control group. The skin cell proliferation percentage of Reference group added with the fetal bovine serum (FBS) was increased by 11.7% through being compared with that of Control group. Therefore, it could prove that the bacterial lysate of the *H. trueperi* TCI66207 strain of the present invention actually had the effect of promoting skin cell proliferation.

Example 5: Genetic Test

Human primary epidermal keratinocytes HPEK-50 (purchased from CELLnTEC company) were cultured in a 6-well culture tray. 2 mL of cell medium (Keratinocyte-SFM 1×, purchased from Thermo company) was added into each well. $1\times10^5$ human primary epidermal keratinocytes were planted in each well. Overnight (24 h) culture was performed in a 37° C. constant-temperature incubator.

Cell gene expression test groups are divided into 2 groups: Experiment group and Control group. Experiment group: according to a proportion of adding 0.01 ML of the sample B (bacterial lysate of TCI66207) into per one milliliter of cell medium, co-culture was performed with the human primary epidermal keratinocytes at 37° C. for 6 h. Then, RNA in the cells was collected for analysis. Control group: the sample B was not added, the human primary epidermal keratinocytes were cultured at 37° C. for 6 h, and then, RNA in the cells was collected for analysis.

After each group was cultured for 6 h, the medium containing the sample B (bacterial lysate of TCI66207) or a pure medium was removed. Washed cells were taken. After the cells were broken by lysate (purchased from UNI-ONWARD company), RNA of the cells in each group was extracted by an RNA extraction reagent kit (purchased from Geneaid company, Taiwan). Next, mRNA transcription was performed by using SuperScript®III reverse transcriptase in combination with the extracted RNA and primers to generate a cDNA product. cDNA was used as a template, and Primer pairs were used for amplifying target genes. The primer pairs were primers (listed in Table I below) of KRT14, HAS3 and TBP (used as Internal reference group). In a StepOne Plus real-time PCR system (ABI), KAPA CYBR FAST qPCR kits (2×) (KAPA Biosystems) were utilized to perform a quantitative real-time reverse transcription polymerase chain reaction test, so as to quantify the mRNA expression levels of KRT14 and HAS3 genes.

The relative expression levels of the target genes were deduced from an equation $2^{-\Delta\Delta ct}$, the relative fold change was calculated by using TBP gene (used as Internal reference group) and a cycle threshold of the reference gene through standard deviation. $\Delta Ct=C_{target\ gene/reference\ gene}-Ct_{TBP}$. $\Delta Ct=\Delta Ct_{target\ gene}-\Delta Ct_{reference\ gene}$. Fold change=$2^{-\Delta\Delta ct}{}_{mean}$. According to a comparison reference, the expression level of the target gene of Reference group was regarded as 1. The statistical significance differences among all tissues were determined through single tailed Student t-test.

TABLE I

| Primer name | Sequence number | Sequence |
| --- | --- | --- |
| KRT14-F | SEQ ID NO: 2 | TTCTGAACGAGATGCGTGAC |
| KRT14-R | SEQ ID NO: 3 | GCAGCTAATCTCCAGGTTC |
| HAS3-F | SEQ ID NO: 4 | CGCAGCAACTTCCATGAGG |
| HAS3-R | SEQ ID NO: 5 | AGTCGCACACCTGGATGTAGT |
| TBP-F | SEQ ID NO: 6 | TATAATCCCAAGCGGTTTGC |
| TBP-R | SEQ ID NO: 7 | GCTGGAAAACCCAACTTCTG |

It should be noted that the relative expression levels of genes in the figures were the expression level of each group calculated by regarding the expression level of Control group as 1. Additionally, the statistical significance differences among all groups were counted and analyzed through Student t-test. In the figures, "*" represented a P value less than 0.05. "" represents a P value less than 0.01. "*" represents a P value less than 0.001. More "*" represents more significant statistical differences.

Figure 4:
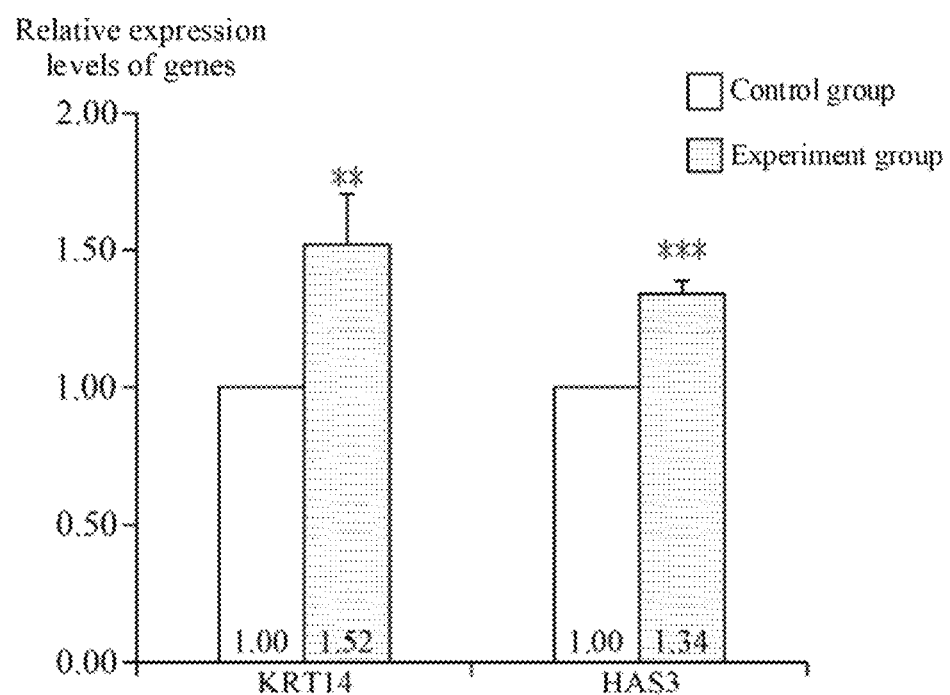
FIG. 4 shows relative expression levels of KRT4 and HAS3 genes of human primary epidermal keratinocytes under conditions of being treated or not being treated by the bacterial lysate of the *H. trueperi* TCI66207 strain.

Results of this experimental example were shown in FIG. 4. Compared with Reference group, the expression levels of KRT14 and HAS3 genes in Experiment group were obviously improved. The bacterial lysate of the *H. trueperi* TCI66207 strain could increase the expression of the KRT74 gene. In detail, when the expression level of the KRT14 gene of Reference group was considered to be 1, the expression level of the KRT14 gene in Experiment group was 1.52. Therefore, the bacterial lysate of the *H. trueperi* TCI66207 strain could maintain keratinocyte arrangement to realize skin collenchyma completeness and further prevent skin moisture loss.

On the other hand, the bacterial lysate of the *H. trueperi* TCI66207 strain could increase the expression of the HAS3 gene. In detail, when the expression level of the HAS3 gene in Reference group was considered to be 1, the expression level of the HAS3 gene in Experiment group was 1.34. Therefore, the bacterial lysate of the *H. trueperi* TCI66207 strain could promote endogenic hyaluronic acid production to maintain skin elasticity and luster.

Example 6: Human Body Experiment

After face cleaning in the morning and evening every day, 8 subjects respectively coated an essence (essence A) containing the bacterial lysate of the *H. trueperi* TCI66207 strain and a placebo onto left and right faces, and performed slight massage with fingers to promote absorption. The experiment lasted 4 weeks. Ingredients of the essence A were mainly 1 vol % of a sample A and 99 vol % of a blank essence. Ingredients of the blank essence included 93.5 vol % of water, 0.6 vol % of SymSave®H (hydroxyacetophenone), 0.6 vol % of hexalene glycol, 5 vol % of 1,3-butanedione, 0.2 vol % of Xanthan gum and 0.1 vol % of triethanolamine.

Detection was respectively performed in the $0^{th}$ week (no coating of the essence A or the placebo) and the $4^{th}$ week (continuous coating of the essence A or the placebo) after use by an instrument (DermaLab® Combo skin analysis instrument).

Figure 5:
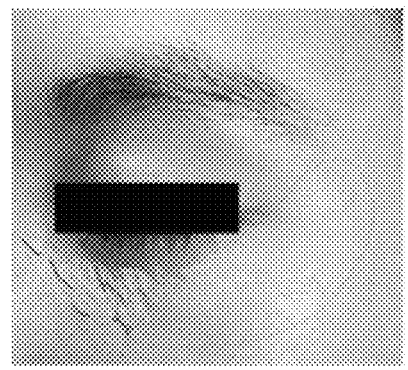
FIG. 5 is an image of face skin of a subject coated with a placebo shot by a detection instrument in the $0^{th}$ week.
Figure 6:
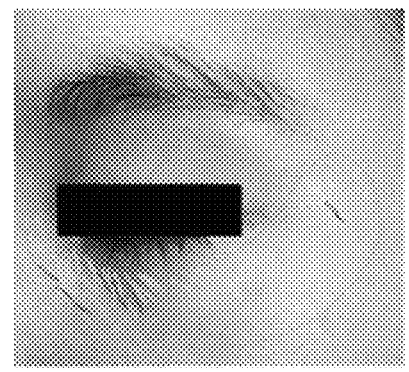
FIG. 6 is an image of face skin of the subject coated with the placebo shot by a detection instrument in the $4^{th}$ week.
Figure 7:
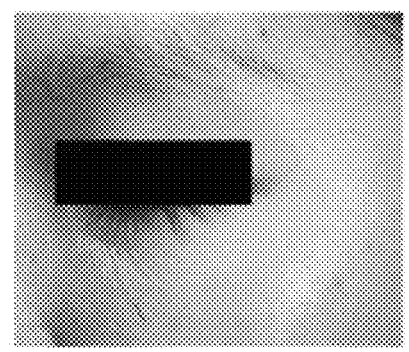
FIG. 7 is an image of face skin of a subject not coated with an essence containing the bacterial lysate of the *H. trueperi* TCI66207 strain shot by a detection instrument in the $0^{th}$ week.
Figure 8:
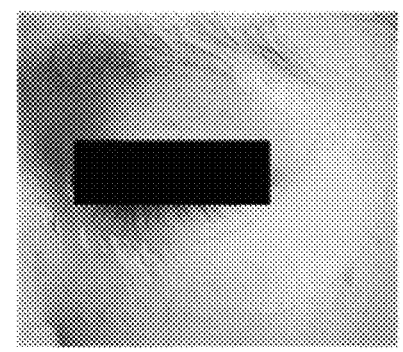
FIG. 8 is an image of face skin of the subject coated with an essence containing the bacterial lysate of the *H. trueperi* TCI66207 strain shot by a detection instrument in the $4^{th}$ week.

Referring to FIG. 5 and FIG. 6, wrinkles under eyes of the subjects coated with the placebo in the $4^{h}$ week (as shown in FIG. 6) relative to the $0^{th}$ week (as shown in FIG. 5) were not obviously reduced or smoothened. Referring to FIG. 7 and FIG. 8, wrinkles under eyes of the subjects coated with the essence A were smoother and sparser in the $4^{th}$ week (as shown in FIG. 8) relative to the $0^{th}$ week (as shown in FIG. 7). Therefore, it could be known that compared with the wrinkle states in the $0^{th}$ week, after the essence containing the bacterial lysate of the *H. trueperi* TCI66207 strain was continuously coated, the wrinkles of the subjects were reduced. In other words, the bacterial lysate of the *H. trueperi* TCI66207 strain had a capability of relieving the wrinkles.

Figure 9:
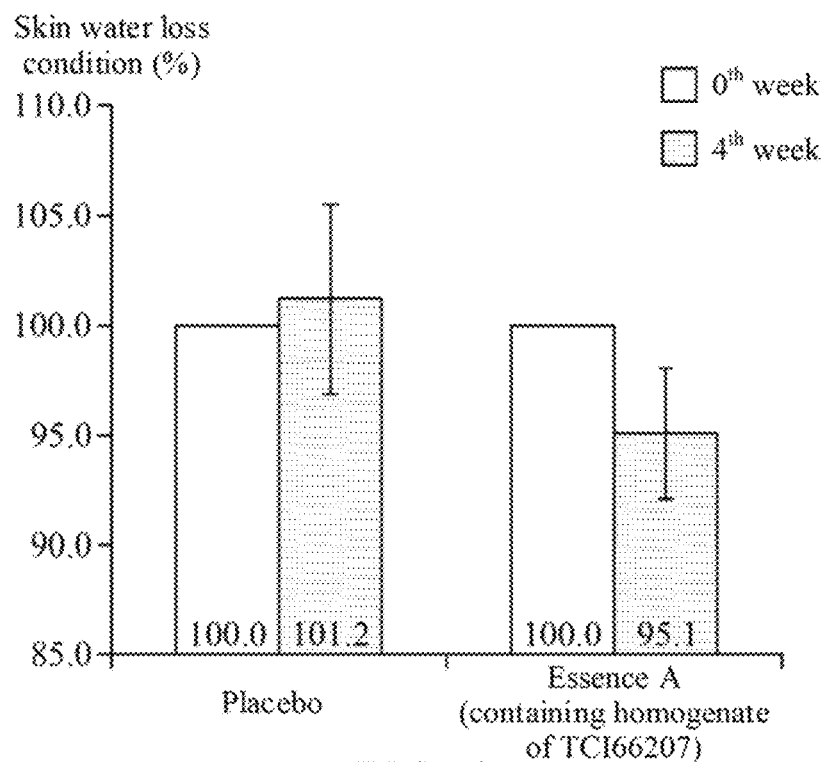
FIG. 9 shows skin water loss conditions of the skin of the subjects coated with a placebo and an essence A containing the bacterial lysate of the *H. trueperi* TCI66207 strain in the $0^{th}$ week and the $4^{th}$ week.
Figure 10:
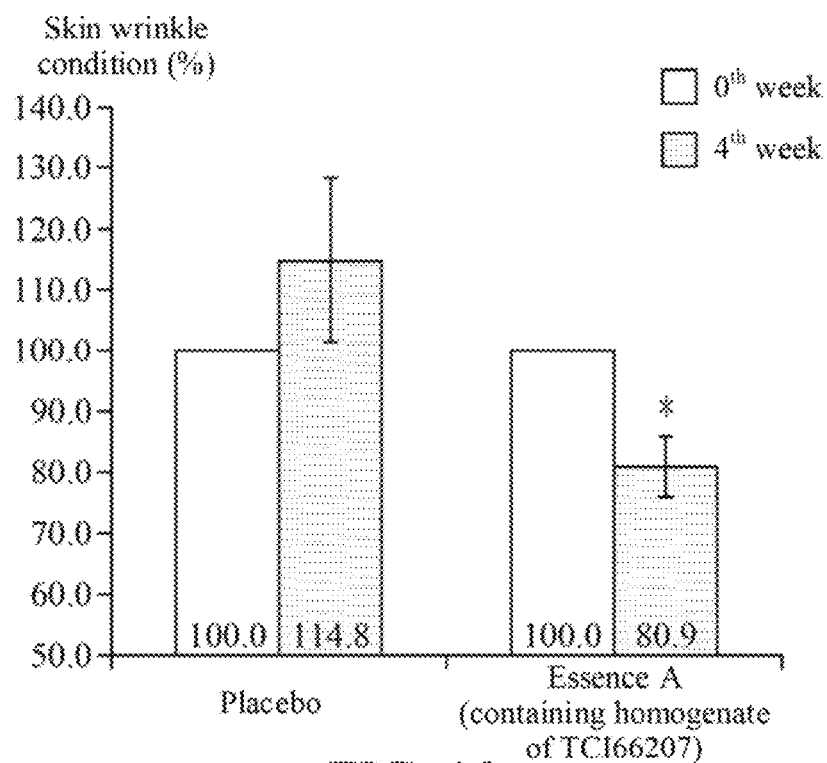
FIG. 10 shows skin wrinkle conditions of the skin of the subjects coated with the placebo and the essence A containing the bacterial lysate of the *H. trueperi* TCI66207 strain in the $0^{th}$ week and the $4^{th}$ week.
Figure 11:
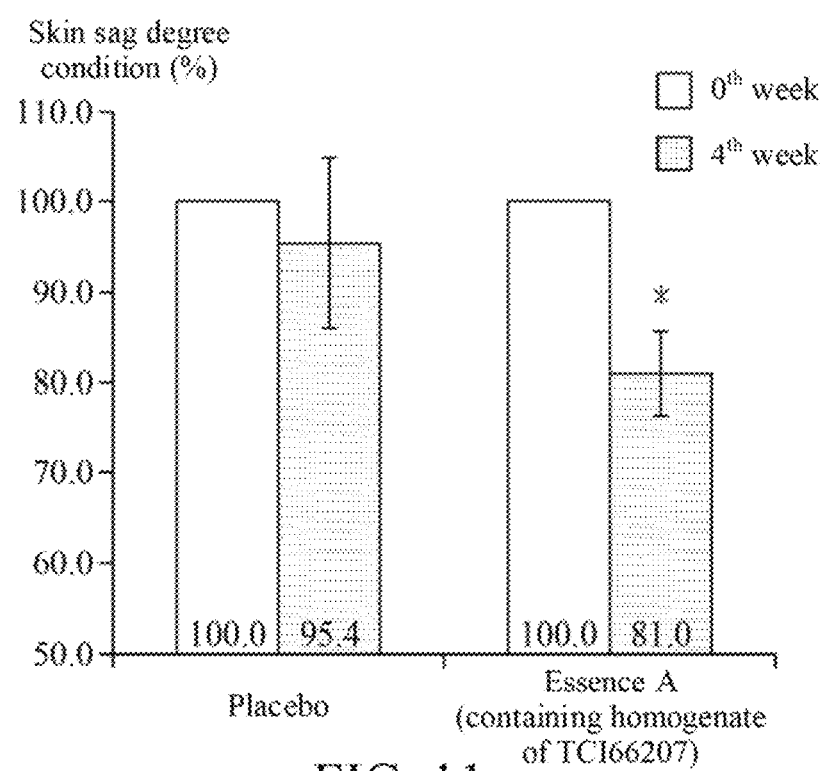
FIG. 11 shows levels of skin sagging conditions of the skin of the subjects coated with the placebo and the essence A containing the bacterial lysate of the *H. trueperi* TCI66207 strain in the $0^{th}$ week and the $4^{th}$ week.

After detection by an instruction (DermaLab® Combo skin analysis instrument), by using the skin condition in the $0^{th}$ week as the reference (i.e., the relative skin condition in the $0^{th}$ week was regarded as 100%), the relative skin condition (%) in the fourth week was calculated. Additionally, the statistical significance differences between the relative skin condition of the $0^{th}$ week and the relative skin condition in the $4^{th}$ week were counted and analyzed by Student t-tests, as shown in FIG. 9 to FIG. 11. In FIG. 9 to FIG. 11, "*" represents a P value less than 005 in comparison with the $0^{th}$ week.

Referring to FIG. 9, the skin water loss condition of the subjects coated with the placebo was improved by 1.2% in the $4^{th}$ week relative to the $0^{th}$ week. However, the skin water loss condition of the subjects coated with the essence A was reduced by 4.9% in the $4^{th}$ week relative to the $0^{th}$ week. That is, after the continuous coating of the essence containing the bacterial lysate of the *H. trueperi* TCI66207 strain, the skin of the subject had a better water-retention capacity.

Referring to FIG. 10, the skin wrinkle conditions of the subjects coated with the placebo was improved by 14.8% in the 4th week relative to the $0^{th}$ week. However, the skin wrinkle conditions of the subjects coated with the essence A was reduced by 19.1% in the $4^{th}$ week relative to the $0^{th}$ week. That is, the wrinkles of the skin of the subjects were relieved after continuous coating of the essence A containing the bacterial lysate of the *H. trueperi* TCI66207 strain.

Referring to FIG. 11, the level of skin sagging of the subjects coated with the placebo was reduced by 4.6% in the $4^{th}$ week relative to the $0^{th}$ week. However, the skin wrinkle condition of the subjects coated with the essence A was reduced by 19.1% in $4^{th}$ week relative to the $0^{th}$ week. That is, after continuous coating of the essence A containing the bacterial lysate of the *H. trueperi* TCI66207 strain, the skin sag condition of the subjects was relieved.

Based on the above, in some embodiments, the bacterial lysate of the *H. trueperi* TCI66207 strain has a function of improving skin cell mitochondrion activity. In some embodiments, the bacterial lysate of the TCI66207 strain has a function of promoting skin cell proliferation. In some embodiments, the bacterial lysate of the TCI66207 strain may increase expression of keratin (Keratin14) gene, thereby providing a function of maintaining skin corneum layer completeness. In some embodiments, the bacterial lysate of the TCI66207 strain may increase expression of hyaluronic acid synthase (HAS3) gene, thereby providing a function of promoting hyaluronic acid production.

What is claimed is:

1. A composition comprising a bacterial lysate of *Halobacillus trueperi* TCI66207 strain, water, hydroxyacetophenone, hexalene glycol, 1,3-butanedione, xanthan gum and triethanolamine, wherein the *H. trueperi* TCI66207 strain is deposited in Leibniz Institute DSMZ-German Collection of Microorganisms and Cell Cultures under an accession number of DSM 33381.

2. The composition according to claim 1, wherein the bacterial lysate improves skin cell mitochondrion activity.

3. The composition according to claim 1, wherein the bacterial lysate promotes skin cell proliferation.

4. The composition according to claim 1, wherein the bacterial lysate maintains the skin corneum layer structure and/or promotes hyaluronic acid production.

5. The composition according to claim 1, wherein the bacterial lysate increases expression of Keratin14 and/or Hyaluronic acid synthase 3 genes.

6. The composition according to claim 1, wherein the composition is a pharmaceutical composition or a cosmetic composition.

* * * * *

SEQUENCE LISTING

<160> NUMBER OF SEQ ID NOS: 7

<210> SEQ ID NO 1
<211> LENGTH: 1487
<212> TYPE: DNA
<213> ORGANISM: Halobacillus trueperi

<400> SEQUENCE: 1

| | | | | | | |
|---|---|---|---|---|---|---|
| gacgaacgct | ggcggcgtgc | ctaatacatg | caagtcgagc | gcgggaagcg | agtggatccc | 60 |
| ttcggggtga | agctcgtgga | acgagcggcg | gacgggtgag | taacacgtgg | gcaacctgcc | 120 |
| tgtaagatcg | gaataacccc | gggaaaccgg | ggctaatgcc | gggtaatact | ttctttcgca | 180 |
| tgaaggaaag | ttgaaagatg | gcttcttgct | atcacttaca | gatgggcccg | cggcgcatta | 240 |
| gctagttggt | gaggtaacgg | ctcaccaagg | cgacgatgcg | tagccgacct | gagagggtga | 300 |
| tcggccacac | tgggactgag | acacggccca | gactcctacg | ggaggcagca | gtagggaatc | 360 |
| ttccgcaatg | gacgaaagtc | tgacggagca | acgccgcgtg | aacgatgaag | gtcttcggat | 420 |
| cgtaaagttc | tgttgttagg | gaagaacaag | taccgtgcga | atagagcggt | accttgacgg | 480 |
| tacctaacga | ggaagccccg | gctaactacg | tgccagcagc | cgcggtaata | cgtaggggc | 540 |
| aagcgttgtc | cggaattatt | gggcgtaaag | cgcgcgcagg | cggttcctta | agtctgatgt | 600 |
| gaaagcccac | ggctcaaccg | tgagggtca | ttggaaactg | gggaacttga | ggacagaaga | 660 |
| ggagagtgga | attccacgtg | tagcggtgaa | atgcgtagat | atgtggagga | acaccagtgg | 720 |
| cgaaggcgac | tctctggtct | gtttctgacg | ctgaggtgcg | aaagcgtggg | tagcaaacag | 780 |
| gattagatac | cctggtagtc | cacgccgtaa | acgatgagtg | ctaggtgtta | ggggcttcc | 840 |
| accccttagt | gctgaagtta | acgcattaag | cactccgcct | ggggagtacg | gccgcaaggc | 900 |
| tgaaactcaa | aggaattgac | gggggcccgc | acaagcggtg | gagcatgtgg | tttaattcga | 960 |
| agcaacgcga | agaaccttac | caggtcttga | catccttgga | catccctaga | gatagggctt | 1020 |
| tcccttcggg | gaccaagtga | caggtggtgc | atggttgtcg | tcagctcgtg | tcgtgagatg | 1080 |
| ttgggttaag | tcccgcaacg | agcgcaaccc | ctaatcttag | ttgccagcat | tcagttgggc | 1140 |
| actctaaggt | gactgccggt | gacaaaccgg | aggaaggcgg | ggatgacgtc | aaatcatcat | 1200 |
| gccccttatg | acctgggcta | cacacgtgct | acaatggatg | gtacaaaggg | cagcgaagcc | 1260 |
| gcgaggtgta | gcaaatccca | taaaaccatt | ctcagttcgg | attgcaggct | gcaactcgcc | 1320 |
| tgcatgaagc | cggaatcgct | agtaatcgcg | gatcagcatg | ccgcggtgaa | tacgttcccg | 1380 |
| ggccttgtac | acaccgcccg | tcacaccacg | agagttggca | acacccgaag | tcggtgaggt | 1440 |
| aaccttttg | gagccagccg | ccgaaggtgg | ggccaatgat | tggggtg | | 1487 |

<210> SEQ ID NO 2
<211> LENGTH: 20
<212> TYPE: DNA
<213> ORGANISM: Artificial Sequence
<220> FEATURE:
<223> OTHER INFORMATION: KRT14 Primer-F

<400> SEQUENCE: 2

| | |
|---|---|
| ttctgaacga gatgcgtgac | 20 |

<210> SEQ ID NO 3
<211> LENGTH: 20
<212> TYPE: DNA
<213> ORGANISM: Artificial Sequence
<220> FEATURE:
<223> OTHER INFORMATION: KRT14 Primer-R

```
<400> SEQUENCE: 3
gcagctcaat ctccaggttc                                                    20

<210> SEQ ID NO 4
<211> LENGTH: 19
<212> TYPE: DNA
<213> ORGANISM: Artificial Sequence
<220> FEATURE:
<223> OTHER INFORMATION: HAS3 Primer-F

<400> SEQUENCE: 4
cgcagcaact tccatgagg                                                     19

<210> SEQ ID NO 5
<211> LENGTH: 21
<212> TYPE: DNA
<213> ORGANISM: Artificial Sequence
<220> FEATURE:
<223> OTHER INFORMATION: HAS3 Primer-R

<400> SEQUENCE: 5
agtcgcacac ctggatgtag t                                                  21

<210> SEQ ID NO 6
<211> LENGTH: 20
<212> TYPE: DNA
<213> ORGANISM: Artificial Sequence
<220> FEATURE:
<223> OTHER INFORMATION: TBP Primer-F

<400> SEQUENCE: 6
tataatccca agcggtttgc                                                    20

<210> SEQ ID NO 7
<211> LENGTH: 20
<212> TYPE: DNA
<213> ORGANISM: Artificial Sequence
<220> FEATURE:
<223> OTHER INFORMATION: TBP Primer-R

<400> SEQUENCE: 7
gctggaaaac ccaacttctg                                                    20
```